(12) United States Patent
Azzaretto

(10) Patent No.: US 6,695,615 B1
(45) Date of Patent: Feb. 24, 2004

(54) DEVICE FOR SEPARATING A DENTITION MODEL FORM A SUPPORTING PLATE

(76) Inventor: Michael Azzaretto, 55 Rue de Metz, F-57470 Hombourg Haut (FR)

(*) Notice: Subject to any disclaimer, the term of this patent is extended or adjusted under 35 U.S.C. 154(b) by 0 days.

(21) Appl. No.: 09/889,337
(22) PCT Filed: Nov. 10, 2000
(86) PCT No.: PCT/DE00/03936
§ 371 (c)(1), (2), (4) Date: Sep. 28, 2001
(87) PCT Pub. No.: WO01/35853
PCT Pub. Date: May 25, 2001

(30) Foreign Application Priority Data

Nov. 17, 1999 (DE) .......................... 199 55 154

(51) Int. Cl.[7] ................................. A61C 9/00
(52) U.S. Cl. ....................................... 433/74
(58) Field of Search ..................... 433/74, 34, 47; 249/67, 68, 70, 74, 54

(56) References Cited

U.S. PATENT DOCUMENTS

| 2,483,093 | A | * | 9/1949 | Harvey | |
|---|---|---|---|---|---|
| 4,439,151 | A | * | 3/1984 | Whelan | 433/60 |
| 4,608,016 | A | * | 8/1986 | Zeiser | 433/74 |
| 4,708,648 | A | * | 11/1987 | Weissman | 433/74 |
| 4,940,409 | A | * | 7/1990 | Nordin | 433/74 |
| 4,954,081 | A | * | 9/1990 | Williams | 433/74 |
| 5,098,290 | A | * | 3/1992 | Honstein et al. | 433/74 |
| 5,738,518 | A | * | 4/1998 | Nowak | 433/74 |

FOREIGN PATENT DOCUMENTS

| DE | 3825014 | 1/1990 |
|---|---|---|
| DE | 9012124 | 8/1990 |
| DE | 29605973 | 6/1996 |

* cited by examiner

*Primary Examiner*—Todd E. Manahan
(74) *Attorney, Agent, or Firm*—Sofer & Haroun, LLP

(57) ABSTRACT

The present invention provides for a device for use with denture models comprised of a supporting plate having upper and lower sides, and having at least one opening located on the upper side. An area for receiving retention pins is provided on the upper side of the supporting plate, the opening being located in the area for receiving the retention pins. At least one fitting head is provided where the fitting head is longer than the depth of the opening.

Figure 1:
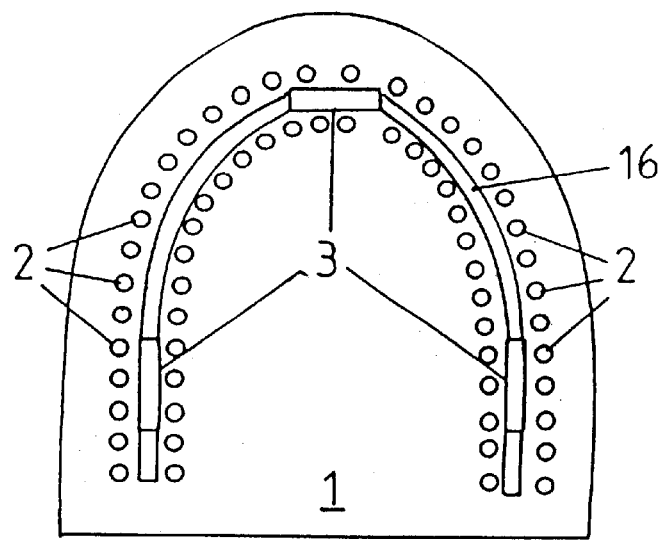

A lift off plate is also provided having upper and lower sides and having a surface capable of contacting the fitting head. The lift off plate has a drilled hole, through which a screw is inserted upwardly from the bottom of the lift off plate, into a screw thread located on the under side of the supporting plate such that the supporting plate is held at a distance from the lift off plate that at least one of the fitting heads, rests on the upper side of the lift off plate so that a denture model, formed on the supporting plate, is removed by pressing the lift off plate upwards against the fitting head.

13 Claims, 3 Drawing Sheets

DEVICE FOR SEPARATING A DENTITION MODEL FORM A SUPPORTING PLATE

The invention relates to a device to lift a denture model off a supporting plate with retention pins.

When a denture model is made, a patient's negative mould is filled with liquid modelling material, e.g. plaster of Paris, and a supporting plate with retention pins is placed on the liquid modelling material so that the free retention pins extend into the modelling material as it hardens. The hardened denture model located on the supporting plate has to be removed from the supporting plate for processing and then replaced later, to prevent the supporting plate from being damaged when, for example, the denture model is cut into separate tooth or jaw segments.

The removal of the hardened denture model from the supporting plate, whether with or without simultaneous removal of the retention pins from the supporting plate, is often difficult, since the hardened modelling material adheres firmly to the supporting plate and the denture model is thus frequently damaged or even broken.

In DBGM 296 05 973, a device for lifting a denture model off its supporting plate is shown.

This device is described for supporting plates in which the retention pins remain in the supporting plate and are not lifted off with the denture model.

Here the device for lifting the denture model off the supporting plate consists of a flat separating section which rests on an additional piece moulded to the centre of the upper surface of the supporting plate. The outer edge of this separating section extends under the inner semicircle of the denture model from the inside.

The supporting plate with the additional moulded-don piece has a hole going through its centre, in which a nut is firmly anchored. This nut serves to hold a lift-off screw. When this screw is screwed in place, its end comes into contact with the flat separating section in which no hole has been drilled and thus lifts it off the rest of the supporting plate. Since the edge of the separating section extends under the denture model from the inside, the separating section takes the whole inner semicircle of the denture model with it and lifts it off the retention pins and supporting plate.

However, the disadvantage of the described device is that the denture model may easily tilt at the retention pins when being lifted off, since pressure is only applied in the middle and not at the places with the greatest adherence. Thus, when the denture model is lifted off the supporting plate, it may crack, e.g. through tensions in the plaster-of-Paris model, and may be damaged or broken.

This present invention tackles the problem of creating a device to lift a denture model off a supporting plate with retention pins, ensuring that, during the lifting-off process, this device exercises an even pressure directly at the places with the greatest adherence, namely directly where the retention pins, which may be either removable or non-removable, extend into the supporting plate, and thus avoiding any tilting or even breakage of-the body of the denture model.

The invention solves this problem with a device to lift a denture model off a supporting plate with retention pins with the features described in the patent claims.

Several alternative versions of the invention are explained and described in greater detail below with the help of drawings.

They show

Figure 2:
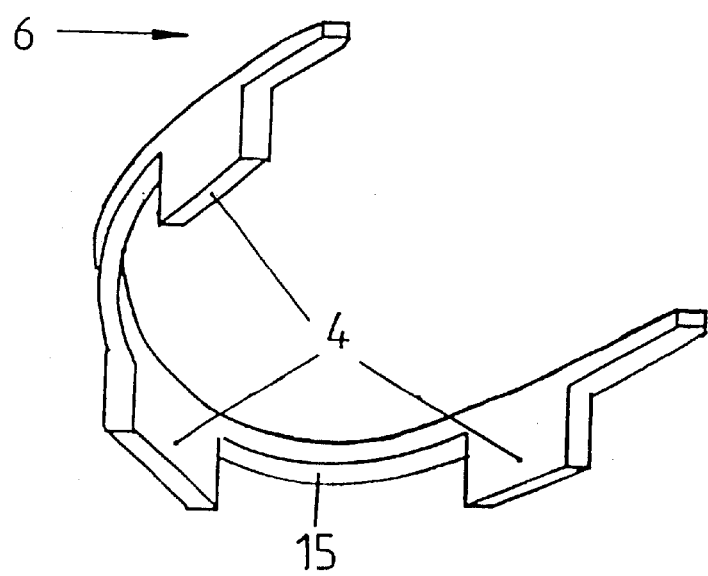
Figure 3:
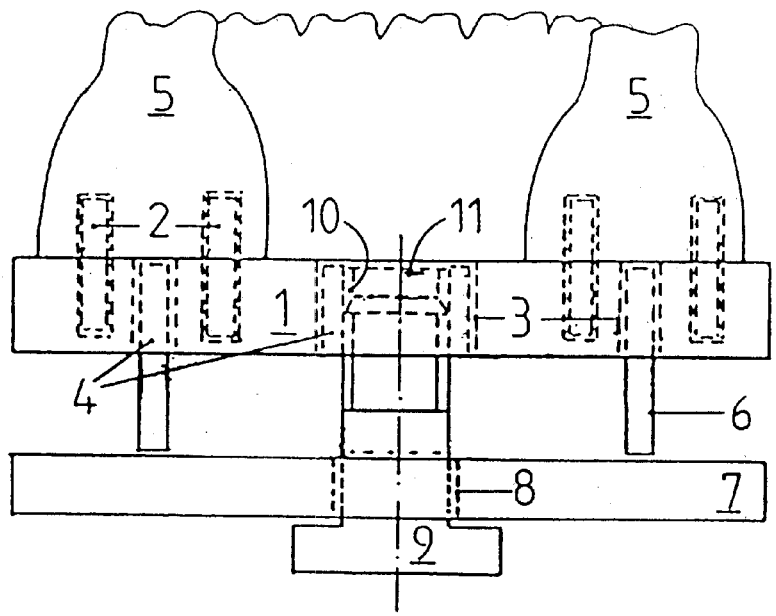
Figure 4:
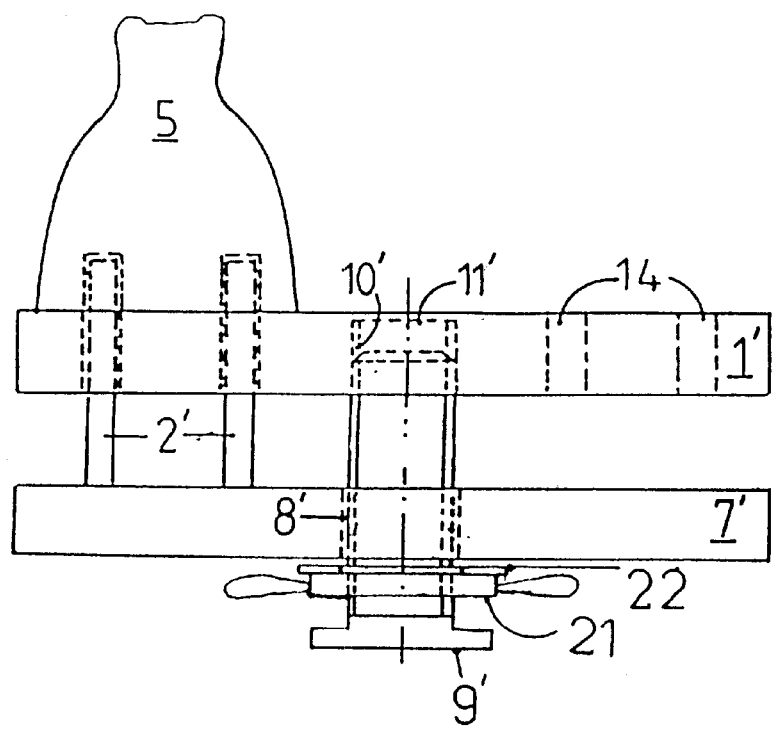
Figure 5:
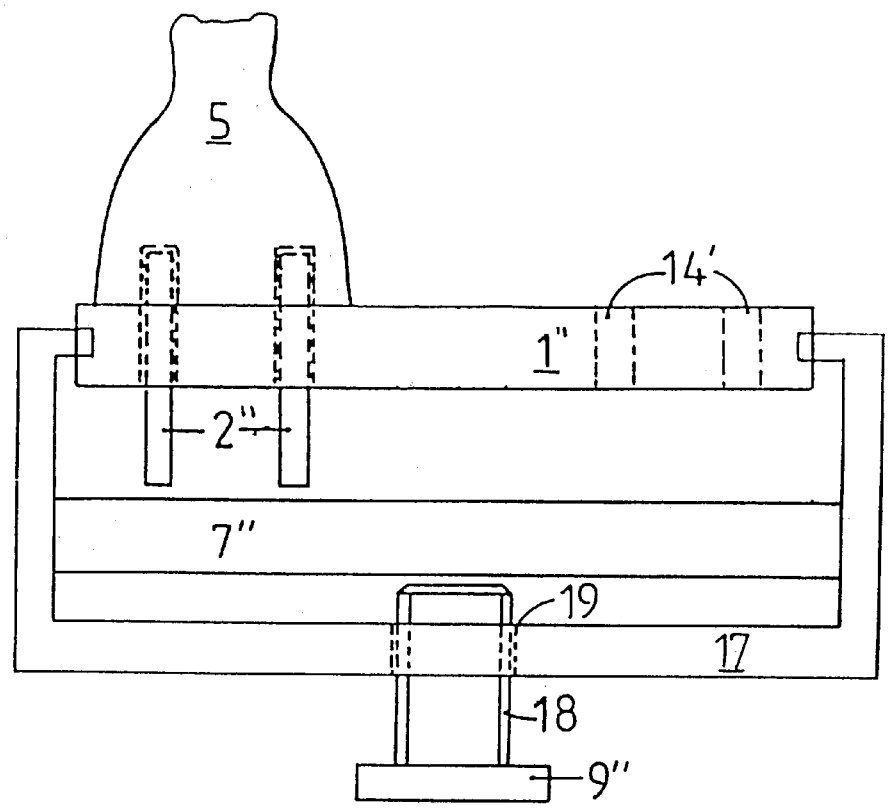
Figure 6:
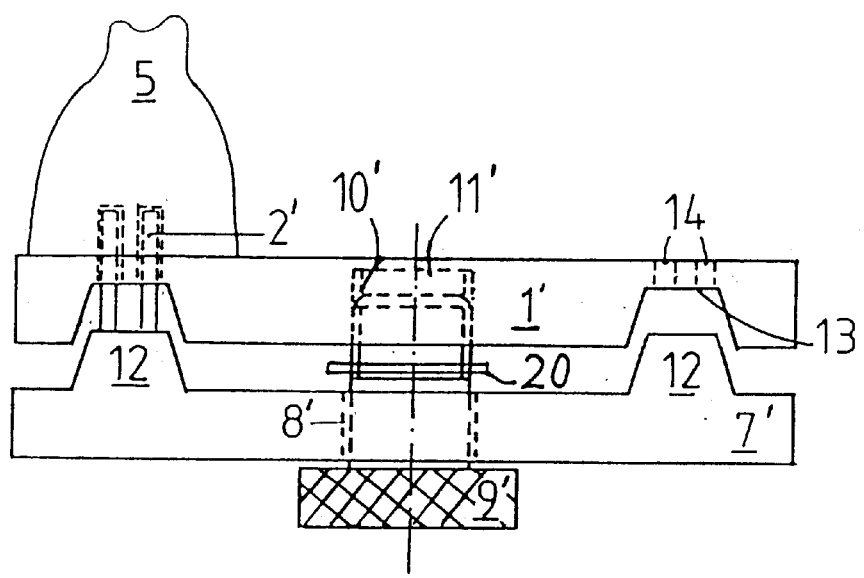

FIG. 1 the top view of a supporting plate with inserted retention pins and openings, of approximately natural size, FIG. 2 a semicircular fitting element, of approximately natural size, FIG. 3 a side view of a supporting plate with a denture model on it and a lift-off plate, with a fitting element positioned between them, of approximately natural size, FIG. 4 a side view of a supporting plate with a denture model on it, retention pins projecting from the bottom of the supporting plate and a lift-off plate, of approximately natural size FIG. 5 a supporting plate with a denture model on it, retention pins projecting from the bottom of the supporting plate, a lift-off plate and a U-shaped clamp, of approximately natural size, and FIG. 6 a side view of a supporting plate with a denture model on it and an indentation at the bottom, from which the retention pins project, and a lift-off plate with an elevation on the top, of approximately natural size.

The device shown in FIG. 1 consists of a supporting plate 1 with numerous retention pins 2, 2, 2, . . . inserted into the top of the supporting plate 1 with their free ends projecting upwards in parallel, these pins being either removable or non-removable. Between the retention pins 2, 2, 2, . . . , which are arranged in two rows, there is an indentation 16 which approximately traces the shape of the rows of retention pins. In this indentation, there are three verticals openings 3, 3, 3, at an equal distance from each other.

FIG. 2 shows a fitting element 6, consisting of an semicircle 15 with three fitting heads 4, 4, 4 at an equal distance from each other. The three fitting heads 4, 4, 4 in the fitting element 6 are pressed from the top of the supporting plate 1 shown in FIG. 1 into the three openings 3, 3, 3 in the supporting plate 1. The three fitting heads 4, 4, 4 are taller than the depth of the openings 3, 3, 3 in the supporting plate 1. The semicircle 15 fits exactly into the indentation 16 in the top of the supporting plate 1.

When the supporting plate 1 with the inserted fitting element 6 and a denture model is placed on a base and vertical pressure is exerted on the supporting plate 1, the fitting element 6 presses on to the bottom of the denture model positioned on the supporting plate 1 so that it is lifted off the supporting plate 1.

The alternative version of the invention pictured in FIG. 3 shows a supporting plate 1 with a denture model 5 and the fitting heads 4, 4, 4 of the fitting element 6 inserted into the openings 3, 3, 3, On the bottom of the supporting plate 1, there is a blind hole 11 with a screw thread 10.

Underneath the supporting plate 1, a lift-off plate 7 is positioned, which has a drilled hole 8 in the centre, through which a screw 9 is run from the bottom of the lift-off plate 7.

The end of the screw is screwed into the blind hole 11 in the bottom of the supporting plate, so that the lift-off plate 7 gradually exerts pressure on the bottom ends of the fitting heads 4, 4, 4, . . . , projecting out of the bottom of the supporting plate 1. These fitting heads, for their part, exert pressure as one fitting element 6 on the bottom of the denture model 5 and lift it off the supporting plate 1 without any tilting.

FIG. 4 shows another device to lift a denture model off a supporting plate with retention pins, in which the pressure to lift the denture model 5 off the supporting plate 1' is exerted directly on the retention pins 2', 2', 2', . . . which are affixed in the denture model 1' and run through the openings 14, 14, 14, . . . in the supporting plate In the centre of the bottom of the supporting plate 1', there is a blind hole 11 with a screw thread 10.

Underneath the supporting plate 1', a lift-off plate 7' is positioned, which has a drilled hole 8' in the centre, through which a screw 9' is run from the bottom of the- lift-off plate 7'.

Between the lift-off plate 7' and the head of the screw 9', there is a wing nut 21 with a washer 22, so that the blind hole 11' in the bottom of the supporting plate 1' need only be very flat and only serves to hold the bottom end of the screw 9'.

By turning the wing nut 21 towards the end of the screw, the lift-off plate 7' is pressed evenly onto the retention pin ends projecting from the supporting plate 1'. The denture model 5 is simply lifted off the supporting plate 1' without any tilting and without causing any tension in the body of the denture model.

FIG. 5 shows another device to lift a denture model off a supporting plate with retention pins, in which a U-shaped clamp 17 is located underneath the lift-off plate 7" and encompasses the lift-off plate 7" and the supporting plate 1" from below and is fastened to the sides of the supporting plate 1" in a removable fashion, e.g. fits into two openings by means of two projecting pieces.

From the bottom of the supporting plate 1", the ends of the retention pins 2", 2", 2", . . . project from the openings 14', 14', 14', . . . and rest on the top of the lift-off plate 7". The U-shaped clamp 17 has a drilled hole 18 through its centre with a screw thread 19, into which a screw 9" is fitted, the bottom end of which rests on the bottom of the lift-off plate 7".

When the screw 9" is turned, it exerts pressure on the lift-off plate 7", which, for its part, presses the retention pins out of the openings 14', 14', 14', . . . and thus lifts off the denture model 5 positioned on the supporting plate 1" without tilting.

FIG. 6 shows a different constructional form of the device shown in FIG. 4, in which the supporting plate 1' has a semicircular indentation 13 in its underside into which the retention pins 2', 2', 2', . . . project.

The lift-off plate 7' has an exactly matching semicircular elevation 12 on its upper side, which lifts the retention pins and the denture model 5 off the supporting plate 1' when the screw 9' is twisted into the blind hole 11' with a screw thread 10'. To hold the screw 9' in the hole 8' in the lift-off plate 7', a flat nut 20 is screwed onto the screw 9'.

The screw 9' should preferably be a knurled thumb screw so that it can be turned easily with one hand.

What is claimed is:

1. A device for use with denture models, said device comprising:
   a supporting plate having upper and lower sides, further having at least one opening located on said upper side,
   an area for receiving retention pins on the upper side of said supporting plate, wherein said opening is located in said area for receiving said retention pins; and
   at least one fitting head where said fitting head is longer than the depth of said opening;
   a lift off plate having upper and lower sides and having a surface capable of contacting said fitting head; and
   said lift off plate having a drilled hole, through which a screw is inserted upwardly from the bottom of said lift off plate, into a screw thread located on the under side of said supporting plate such that said supporting plate is held at such a distance from said lift off plate that at least one of said fitting heads, rests on the upper side of said lift off plate such that a denture model, formed on said supporting plate, is removed by pressing said lift off plate upwards against said fitting head.

2. A device as claimed in claim 1 wherein said opening is a conically narrowing opening.

3. A device as claimed in claim 1, wherein said opening is a cylindrical opening.

4. A device as claimed in claim 1 wherein said device further comprises a u-shaped clamp having a bottom surface and lateral arms extending from said surface, said lateral arms fastened to the sides of said supporting plate and where the bottom surface is disposed below the lower side of said lift off plate;
   said bottom surface of said u-shaped clamp having a screw thread, with a screw placed therein that extends upwardly through to the bottom of the lift off plate such that turning of the screw presses said lift off plate towards said supporting plate and thus presses upwardly on said fitting heads to remove said denture model.

5. A device as claimed in claim 1, wherein said upper side of said supporting plate further comprises a first upper indentation located in said area for receiving retention pins,
   and where at least two fitting heads are connected so as to form a continuous fitting element, such that the connecting portion of said fitting element rests in said first upper indentation.

6. A device as claimed in claim 1, wherein the underside of said supporting plate maintains at least one second lower indentation in such a location that said fitting head, extending through said opening, extend outwardly from said supporting plate into said second lower indentation; and
   wherein said upper side of said lift off plate has a corresponding elevation spaced opposite said second lower indentation such that when said lift off plate is pressed upwardly against said support plate said elevation moves into said second lower indentation and presses against the bottom of said fitting heads.

7. A device for use with denture models, said device comprising:
   a supporting plate having upper and lower side, further having at least one opening located on the upper side,
   at least one retention pin located in said at least one opening, wherein said retention pin extend through said opening and extends both above and below the surfaces of said supporting plate;
   a lift off plate having upper and lower sides and having a surface capable of contacting said retention pin, said lift off plate having a drilled hole, through which a screw is inserted upwardly from the bottom of said lift off plate, into a bind hole, located on the under side of said supporting plate such that said supporting plate is held at such a distance from said lift off plate that at least one of said retention pins, rests on the upper side of said lift off plate.

8. A device as claimed in claim 7, wherein the underside of said supporting plate maintains at least one second lower indentation in such a location that said retention pins, extending through said opening extends outwardly to said second lower indentation; and
   wherein said upper side of said lift off plate has a corresponding elevation spaced opposite said second lower indentation such that when said lift off plate is pressed upwardly against said support plate said elevation moves into said second lower indentation and presses against the bottom of said retention pins.

9. A device as claimed in claim 1 or 7, further comprising a wing nut and a washer disposed on the screw thread of said screw between said lift off plate and said supporting plate and the head of said screw.

10. A device as claimed in claim 1 or 7, wherein said screw located between said lift off plate and said supporting plate further comprises a nut for holding said screw in said hole in said lift off plate.

11. A device for use with denture models, said device comprising:

a supporting plate having upper and lower side, further having at least one opening located on the upper side, at least one retention pin located in said at least one opening, wherein said retention pin extend through said opening and extends both above and below the surfaces of said supporting plate;

a lift off plate having upper and lower sides and having a surface capable of contacting said retention pins; and a u-shaped clamp having a bottom surface and lateral arms extending from said bottom surface, said lateral arms fastened to the sides of said supporting plate and said bottom surface being disposed below the lower side of said lift off plate such that said supporting plate is held at such a distance from said lift off plate that at least one of said retention pins, rests on the upper side of said lift off plate, wherein said bottom surface of said u-shaped clamp, having a screw thread with a screw placed therein that extends upwardly through to the bottom of the lift off plate such that turning of the screw presses said lift off plate towards said supporting plate and thus presses upwardly on said retention pins, removing said denture model.

12. A device as claimed in claim 11, wherein the underside of said supporting plate maintains at least one second lower indentation in such a location that said retention pins, extending through said opening extends outwardly to said second lower indentation; and wherein said upper side of said lift off plate has a corresponding projection spaced opposite said second lower indentation such that when said lift off plate is pressed upwardly against said support plate said elevation moves into said second lower indentation and presses against the bottom of said retention pins.

13. A device as claimed in claims 1, 4, 7, or 11, wherein said screw is a knurled thumb screw.

\* \* \* \* \*